United States Patent [19]

Helms et al.

[11] 4,256,093

[45] Mar. 17, 1981

[54] PROSTHETIC URINARY SPHINCTER

[75] Inventors: Curtis R. Helms; Harold M. Smyly, both of Huntsville, Ala.

[73] Assignee: The United States of America as represented by the Administrator of the National Aeronautics and Space Administration, Washington, D.C.

[21] Appl. No.: 950,877

[22] Filed: Oct. 12, 1978

[51] Int. Cl.[3] .......................... A61B 19/00; A61F 1/00
[52] U.S. Cl. .................................... 128/1 R; 128/346; 128/DIG. 25; 137/493
[58] Field of Search ............... 128/1 R, 346, DIG. 25; 137/493

[56] References Cited

U.S. PATENT DOCUMENTS

| 2,455,859 | 12/1948 | Foley | 128/346 |
|---|---|---|---|
| 2,533,924 | 12/1950 | Foley | 128/346 |
| 3,854,469 | 12/1974 | Giori et al. | 128/1 R |
| 3,863,622 | 2/1975 | Buuck | 128/1 R |
| 4,064,882 | 12/1977 | Johnson et al. | 128/349 BV |
| 4,167,952 | 9/1979 | Reinicke | 128/1 R X |

OTHER PUBLICATIONS

Timm et al.–IEEE Transact. Bio–Med. Engr., Oct. 1970, p. 352.

*Primary Examiner*—Dalton L. Truluck
*Attorney, Agent, or Firm*—J. H. Beumer; J. R. Manning; L. D. Wofford, Jr.

[57] ABSTRACT

A pump/valve unit for controlling the inflation and deflation of a urethral collar in a prosthetic urinary sphincter device is disclosed including a compressible bulb pump defining a reservoir made integral with a valve unit for implant wherein the valve unit includes a movable valve member operable by depression of a flexible portion of the valve unit housing for controlling fluid flow between the reservoir and collar and a pressure sensing means which operates the valve member to relieve an excess pressure in the collar should too much pressure be applied by the patient.

4 Claims, 4 Drawing Figures

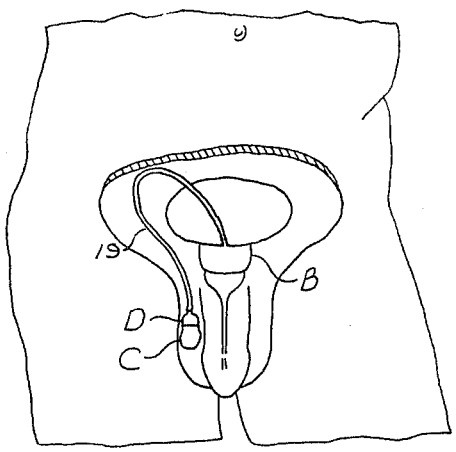
Fig. 1
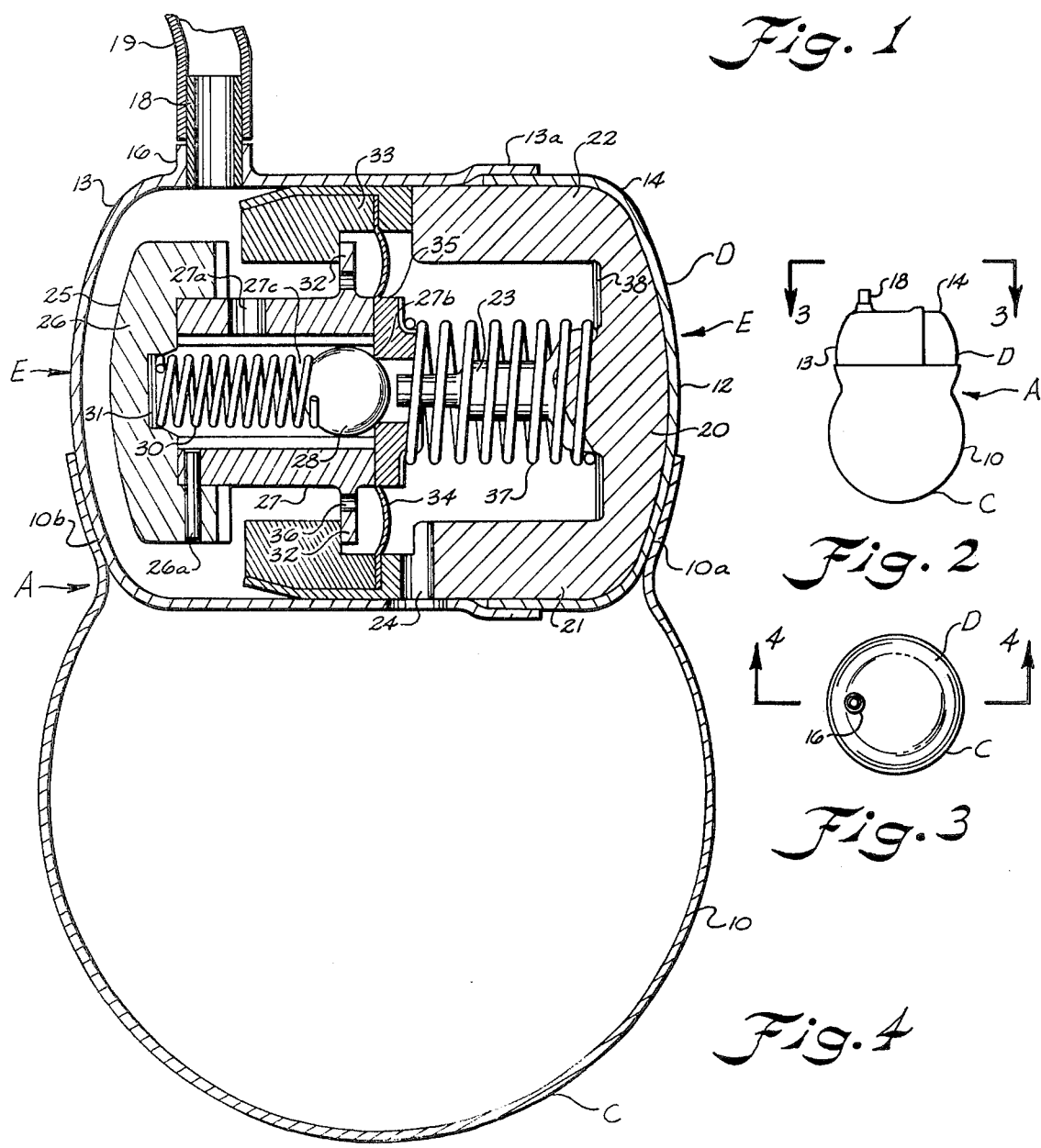
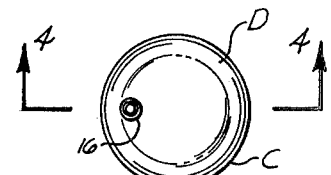
Fig. 2
Fig. 3
Fig. 4

PROSTHETIC URINARY SPHINCTER

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The invention relates to a prosthetic urinary sphincter device for controlling the bladder function in the situation where a person has lost bladder control. Implantable devices have been used before for controlling the bladder functions such as shown in U.S. Pat. No. 3,863,622 which typically include an inflatable cuff surrounding the urethric tube, an inflating pump connected to the cuff for pressurizing the cuff, and a separate deflating pump for removing fluid from the cuff enabling relief of the bladder. A reservoir containing a suitable fluid solution such as a saline solution is connected to the inflating and deflating pumps and check valves are used to control the flow direction. However, this device is not used in extensive application due to the frequent failure of the device and the extensive surgery required for implanting the device, the failure rate being caused primarily by the pump structure and the existence of numerous check valves in the fluid lines. A similar device is shown in U.S. Pat. No. 3,744,063 including separate inflating and deflation pumps wherein the pumps and valves are arranged so that the inflation and deflation are carried out in incremental steps whereby pressure is graduated and controlled.

U.S. Pat. Nos. 3,903,894 and 3,854,469 disclose other implantable devices utilizing bulb reservoirs and flap and slit valves, respectively, which are simple requiring minimum surgery but which do not afford highly accurate pressure control and relief.

U.S. Pat. Nos. 2,455,859 and 2,533,924 typify a second type of artificial sphincter device for controlling urinary incontinence in which the device for controlling inflation of the urethral cuff is not implanted, thus permitting a more conventional construction.

Accordingly, an important object of the present invention is to provide a prosthetic sphincter device for controlling urinary incontinence which is reliable and does not require replacement following implant.

Another important object is a simplified device whose implant requires a minimum amount of surgery.

Still another important object of the present invention is to provide a prosthetic sphincter device which has an improved pump/valve unit for controlling pressurization of the urethral collar.

Yet another important object is the provision of a prosthetic urinary sphincter device having automatic and highly accurate relief of an excess pressure exerted on the urethra due to over pressurization by the user avoiding tissue damage thereto.

SUMMARY OF THE INVENTION

The invention provides a novel unitary press bulb pump/valve device which eliminates the use of two pumps. The device includes a press bulb which acts as a reservoir for containing the fluid and an integral valve unit for controlling the flow direction and manual relief for patient urination. The device further includes a relief feature for controlling the maximum pressure exerted by the urethral collar against the urethra.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein:

FIG. 1 is an elevation illustrating the implant of a prosthetic sphincter device according to the invention;

FIG. 2 is an elevation of a pump/valve unit constructed according to the invention for inflating and deflating a urethral collar of a prosthetic sphincter device;

FIG. 3 is a top plan view of the device of FIG. 2; and

FIG. 4 is an enlarged elevation in cutaway form illustrating in detail a pump/valve unit constructed in accordance with the invention.

DESCRIPTION OF A PREFERRED EMBODIMENT

The drawing illustrates a device, designated generally as A, for pressurizing and relieving the collar B, of a urinary prosthetic sphincter device. The device includes a compressible bulbous pump means C, having a press bulb 10 made from a soft synthetic material such as a silicon elastomer which provides a reservoir for a suitable fluid solution which is used as a pressurizing fluid, such as a saline solution and an integral valve unit D, having a housing 12 which encloses the components thereof. The housing 12 is illustrated as being cylindrical in shape consisting of a cap portion 13 and a base portion 14 received within a flange portion 13a of the cap which may be bonded or welded. The reservoir bulb material 10 is made integral with the housing 12 preferably by bonding at 10a and 10b by any suitable bonding agent which is biocompatible. The cap 13 includes a bulb fitting 16 and boss 18 providing a fluid port for interfacing with the pressurization tubing 19 connected to the urethral collar B. The pressurization tubing 19 may be made of any suitable tubing material such as expanded Teflon.

Internally of the housing 12, the device D has as its components a main body portion 20 which may be of stainless steel and provides a member for retaining the shape of the device generally. The body 20 includes two upstanding leg portions 21 and 22 and a central upstanding stem portion 23 which serves as a valve stem. A fluid port 24 is provided in the upstanding leg portion 21 communicating with the fluid reservoir 10.

A reciprocating valve member 25 is included within the housing and includes a depressible button member 26 which serves as a valve actuator and a valve body 27 attached to the button 26 by means of pin 26a. The housing 12 is made from a suitable resilient material such as silicone elastomer such that the center of cap portion 13 is depressible to manually operate valve actuator button 26 by squeezing the housing between the thumb and finger at arrows E when implanted.

The valve body 27 includes a fluid port 27a, a valve seat 27b defining a second fluid port, and a bore 27c connecting the two ports. A valve element is provided in the form of a ball poppet 28 maintained on the seat 27b by a biasing spring 30. The bias of spring 30 may be adjusted by adding or subtracting shims 31 between button member 26 and the end of spring 30. The poppet valve element thus has a first position off the seat permitting flow through the valve member and a second position on the seat blocking flow therethrough. A flow path exists between the reservoir 10 and collar B when valve element 28 is in its first position through port 24, valve bore 27c, and port 16 of the valve unit.

A pair of outwardly extending flanges 32 cooperate with a cylindrical retainer body portion 33 of the main body 20 to limit the upward vertical movement of the valve member 25. A flexible diaphragm 34 is attached at one end between the retainer body 33 and main body 20 and is partially carried by valve member 25 by attachment at a diaphragm seat member 35 integral with member 25.

The diaphragm 34 divides the interior of housing 12 into a first compartmented section 12a in fluid communication with collar B and a second compartmented section 12b in fluid communication with reservoir 10. The outwardly extending flanges 32 include openings 36 through which the pressure of the fluid in section 12a and hence collar B is transmitted for relieving the pressure should it exceed a predetermined value. Action of the excessive pressure against the diaphragm 34 causes the valve member 25 to move downwardly engaging the ball poppet against the plunger 23 to open the valve and allow the excessive pressure to be relieved, the action against the diaphragm will allow the valve member to raise back to its normal position abutting the retaining member 33 allowing the ball poppet to seat once again.

A spring 37 biases the valve body 27 in its normal position wherein flange 32 abutts the retaining member 33 away from the base 20. The amount of bias of spring 37 may be adjusted by adding or removing annular shims 38 received over stem 23.

The amount of pressure differential across the diaphragm 34 required to unseat ball poppet 28 being a function of the combination of spring bias force provided by springs 31 and 37 whereby the amount of spring bias may be adjusted so as to relieve a desired, predetermined excess of pressure in section 12a and hence collar B. The amount of pressure being limited to that value necessary to close off the urethral passage while avoiding deterioration of the tissue cells as can result from poor blood circulation due to maintenance of an excess pressure on the urethra.

Thus, it can be seen that an advantageous construction for an implantable pump/valve device can be had according to the invention for controlling the inflation and deflation of a urethral collar in an artificial sphincter device which is simple and reliable, requiring a minimum of implant area and surgery and which automatically and accurately relieves an excess of pressure placed upon the urethra by over inflation of the collar by the user avoiding permanent damage to the tissue of the urethra.

While a preferred embodiment of the invention has been described using specific terms, such description is for illustrative purposes only, and it is to be understood that changes and variations may be made without departing from the spirit or scope of the following claims.

What is claimed is:

1. In a prosthetic sphincter device for controlling urinary incontinence of the type having an inflatable urethral collar for surrounding the urethra and preventing flow in the urethral passage when inflated while permitting flow when deflated, a pump/valve unit for inflating and deflating said collar comprising:
    a compressible bulbous pump means having an interior space defining a fluid reservoir;
    a valve unit integral with said bulbous pump means which includes:
        a valve housing having a resilient depressible portion;
        said valve housing having a first port communicating with said fluid reservoir and a second port adapted for connection to said inflatable collar;
        a fluid flow path in said valve housing between said first and second ports;
        a valve member enclosed within said housing disposed in said fluid flow path having a valve actuator element operable by depression of said resilient portion of said valve housing;
        said valve member including a valve element having a first position permitting fluid flowthrough said valve member and a second position blocking fluid flow therethrough; and
        said valve element occupying said first position in response to the compression of said pump means allowing fluid to flow from said reservoir to said inflatable collar and in response to said operation of said actuator element allowing fluid to flow from said collar to said reservoir.

2. The structure of claim 1 wherein said valve unit includes pressure sensing and relief means for sensing the pressure of said fluid in said inflatable collar and causing said valve element to move to said first position in the event said fluid pressure in said collar exceeds a predetermined amount.

3. The structure of claim 1 wherein said valve unit includes:
    base means having an upstanding stem,
    said valve member being carried for movement toward said base means affording engagement between said stem and valve element, and
    biasing means carried between said base means and said valve member urging said valve member away from said base means.

4. The structure of claim 1 wherein said valve member includes:
    a valve body having a fluid port,
    a valve seat formed in said valve body remote from said fluid port defining a second fluid port;
    a bore formed in said valve body connecting said first and second ports,
    said valve element carried in said bore seatable on said valve seat in said second position, and
    said valve actuator element carried by an end of said valve body opposite said valve seat.

* * * * *